(12) United States Patent
Agostini et al.

(10) Patent No.: US 9,737,581 B2
(45) Date of Patent: Aug. 22, 2017

(54) COMPOSITIONS CONTAINING RESVERATROL AND ESSENTIAL OIL OF CLOVES FOR THE TREATMENT OF ITCHING

(75) Inventors: Alida Agostini, Coriano (IT); Sonia Balzi, Coriano (IT)

(73) Assignee: DIFASS INTERNATIONAL S.R.L., Prato (PO) (IT)

( * ) Notice: Subject to any disclaimer, the term of this patent is extended or adjusted under 35 U.S.C. 154(b) by 238 days.

(21) Appl. No.: 14/116,394

(22) PCT Filed: May 10, 2012

(86) PCT No.: PCT/EP2012/058647
§ 371 (c)(1),
(2), (4) Date: Nov. 21, 2013

(87) PCT Pub. No.: WO2012/156275
PCT Pub. Date: Nov. 22, 2012

(65) Prior Publication Data
US 2014/0079835 A1    Mar. 20, 2014

(30) Foreign Application Priority Data

May 19, 2011   (IT) ............................... MI2011A0887

(51) Int. Cl.
*A61K 36/61*     (2006.01)
*A61K 31/05*     (2006.01)
*A61K 45/06*     (2006.01)
*A61K 9/00*      (2006.01)

(52) U.S. Cl.
CPC ............ *A61K 36/61* (2013.01); *A61K 9/0014* (2013.01); *A61K 31/05* (2013.01); *A61K 45/06* (2013.01)

(58) Field of Classification Search
None
See application file for complete search history.

(56) References Cited

U.S. PATENT DOCUMENTS 6,270,780 B1 *   8/2001   Carson et al. ................ 424/401

FOREIGN PATENT DOCUMENTS

CN            101455724 A   *   6/2009

OTHER PUBLICATIONS

Starlife: Revive Night Cream, 2009, p. 9, XP002664790.
Rhonda Allison: Grape Seed Parfait Mask, 2005, XP002664791.
International Search Report issued in counterpart PCT Application No. PCT/EP2012/058647, Aug. 7, 2012.
Written Opinion of International Searching Authority issued in counterpart PCT Application No. PCT/EP2012/058647, Aug. 7, 2012.

* cited by examiner

*Primary Examiner* — Chris R Tate
*Assistant Examiner* — Randall Winston
(74) *Attorney, Agent, or Firm* — Silvia Salvadori, P.C.; Silvia Salvadori

(57) ABSTRACT

The present invention relates to a patch or sticking plaster formulation containing a combination of resveratrol or derivatives thereof and essential oil of cloves (*Eugenia caryophyllata*) for the treatment of itching.

5 Claims, No Drawings

COMPOSITIONS CONTAINING RESVERATROL AND ESSENTIAL OIL OF CLOVES FOR THE TREATMENT OF ITCHING

This application is a U.S. national stage of PCT/EP2012/058647 filed on May 10, 2012, which claims priority to and the benefit of Italian Application No. MI2011A000887 filed on May 19, 2011, the contents of which are incorporated herein by reference in their entirety.

SUMMARY OF THE INVENTION

In a general aspect thereof, the present invention relates to a composition in patch or sticking plaster form containing a combination of resveratrol or derivatives thereof and essential oil of cloves, for the treatment of itching.

TECHNICAL BACKGROUND

Itching is an unpleasant, complex skin sensation which evokes the reflex response of scratching or the desire to scratch. The act of scratching arises as a protective reflex, and leads to the formation of a skin lesion.

Itching is a frequent disorder, although it is generally considered a benign symptom, and can have adverse effects on the patient's well-being and quality of life, and even become disabling when it is severe (1). As it was long considered to be a sub-type of pain, no attention was paid to its neurobiological aspects. Recent studies have demonstrated that itching has a different pathophysiology from pain, and does not have a parallel trend to the underlying disorder. It involves a series of dermatological conditions, but can also be a marker for a systemic disorder. Itching has been classified as follows: cutaneous, neuropathic, neurogenic and psychogenic.

Cutaneous itching is caused by inflammation of the skin, neuropathic itching originates from a nerve lesion, and neurogenic itching originates at central level with no evidence of a neurone disease, as in the case of cholestasis. Finally, psychogenic itching is present in states of delirium (2). Itching is in any event a subjective sensation, and an exhaustive nosographic classification has not yet been developed.

Localised itching is usually caused by dermatosis, with well-defined identifiability and clinical characteristics, such as urticaria, lichen planus, scabies and pediculosis, psoriasis, atopic or contact dermatitis, seborrhoeic dermatitis and lichen simplex.

As regards the treatment of itching, it is generally recommended that the skin should be kept cool and well hydrated, because the intensity of itching increases with body temperature and skin dryness. Topical products based on capsaicin are used for localised itching, and TENS and CFS (cutaneous field stimulation) are also used in resistant cases. Antihistamines are not usually very effective unless the itching is mainly mediated by histamine, as in the case of urticaria (4). In fact, recent studies have demonstrated that histamine is not the main mediator of itching, which is why the efficacy of antihistamines is low (5).

These medicaments present adverse effects on the heart and liver (to a lesser degree and with lower sedative effects in the case of second-generation antihistamines). They must therefore be prescribed cautiously to patients with liver failure or at risk of cardiac arrhythmia.

Topical and systemic corticosteroids are not anti-itching drugs, and are only effective in alleviating part of the itching resulting from inflammatory alterations of the skin. These drugs also have serious side effects, mainly associated with their long-term use or abrupt termination of the treatment: they can cause damage to the gastric mucosa, accumulation of fat on the face and neck, muscle thinning, osteoporosis, hyperglycaemia, reduction in resistance to infection, increased wound-healing time, etc.

Oral doxepin, a tricyclic antidepressant, is a potent anti-itching agent, but must be prescribed with great care, especially for patients with cardiovascular and liver disease, initially at low doses, and must not be abruptly terminated, nor prescribed together with other antidepressants, antibiotics or antifungals. Other antidepressants, such as selective serotonin reuptake inhibitors (SSRIs), and antiepileptics, such as gabapentin, are also used (4). In these cases, the adverse effects are headache, nausea, vertigo, drowsiness, irritability, tremors, etc.

In this scenario, it is unsurprising that anti-itching treatments must be considered "immature", and the choice of therapeutic options still limited.

There is consequently a strongly felt need for an itching treatment which is minimally invasive, devoid of adverse effects, perfectly tolerated by the largest possible number of people and, at the same time, effective and active in a short time, these latter characteristics being essential to ensure compliance by patients, in view of the discomfort caused by a symptom like itching.

A therapeutic option with these characteristics would be particularly indicated in all cases of localised short-term itching, conditions in which aggressive treatments not lacking in side effects and contraindications would not be very advantageous, with a high risk/benefit ratio.

An anti-itching composition consisting of a combination of resveratrol, glycyrrhizic or glycyrrhetinic acid and artemisinin obtained from *Artemisia annua* ("ginghaosu") is described in Chinese patent CN101829130.

French patent FR 2 873 025 describes a patch based on resveratrol.

Chinese patent application CN 10189130 describes topical formulations of resveratrol for the treatment of skin diseases.

However, the combination of resveratrol with eugenol or extracts containing it has not been described to date.

DESCRIPTION OF THE INVENTION

It has now surprisingly been found that the combination of resveratrol or derivatives thereof and essential oil of cloves (*Eugenia caryophyllata*; clove oil) exerts an intense, rapid, long-lasting anti-itching effect. The present invention therefore relates to compositions for the treatment of itching which contain, as active ingredient, a combination of resveratrol or a derivative thereof and essential oil of *Eugenia caryophyllata* (essential oil of cloves; clove oil).

According to a preferred aspect, the compositions of the invention will contain the active ingredients within the following percentage intervals by weight/volume:
a) resveratrol or a derivative thereof: 0.01% to 10%;
b) essential oil of *Eugenia caryophyllata:* 0.02% to 2%.

According to a more preferred aspect, the compositions of the invention will contain the active ingredients within the following percentage intervals by weight/volume:
a) resveratrol or a derivative thereof: 0.05% to 1%;
b) essential oil of *Eugenia caryophyllata:* 0.01% to 0.2%.

In the ambit of the present description and the subsequent claims, the term resveratrol, also known as 3,4',5 trihydroxystilbene and 3,4',5 stilbenetriol, indicates both resveratrol properly so called (IUPAC name: 5-[(E)-2-(4-hydroxyphenyl)-ethenyl]benzene-1,3-diol; or 3,5,4'-trihydroxystilbene; CAS number 501-36-0), and the trans-resveratrol, cis-resveratrol stereoisomeric forms, or 3,4',5-stilbenetriol, 3,4',5-trihydroxystilbene, 3,5,4'-trihydroxystilbene, esters, glycosides and 3'-oxyresveratrol.

Resveratrol is a polyphenolic flavonoid with a stilbene structure, present in plants like Vitaceae, mulberry, red wine, pine, eucalyptus, Polygonaceae, Liliaceae and pulses, peanuts and rhubarb. Resveratrol can also be extracted from *Polygonum cuspidatum*, a plant used in traditional Oriental medicine for dermatitis, arteriosclerosis, hyperlipidaemia and inflammatory disorders. The properties of resveratrol of interest for the purposes of the invention include its anti-inflammatory effect: it inhibits the activity of cyclooxygenase in vivo; reduces chemically-induced oedema, inflammation of the airways induced by lipopolysaccharide and osteoarthritis, and helps to prevent post-transplant rejection (6). When administered intravenously, resveratrol reduces inflammation induced by ischaemia (6). Another effect of resveratrol observed in vivo is its analgesic effect (7-9). According to the literature, resveratrol has an antinociceptive action with action mechanisms which have only partly been clarified, involving neurone protection, inhibition of the oxygenase cycle and opening of the calcium-dependent and voltage-sensitive potassium channels.

Essential oil of *Eugenia caryophyllata* (essential oil of cloves; clove oil) is characterised by antioxidant, antimicrobial, anti-inflammatory and analgesic properties (10). Its anti-inflammatory activity has been demonstrated as prevention of the swelling and redness caused by carrageenans, substances that promote inflammation in preclinical models (11).

According to a further aspect of the invention, the compositions in question may contain other active ingredients, with a complementary action or in any event useful to perfect the anti-itching effect. Examples of these additional ingredients are polidocanol and menthyl lactate (menthol).

The compositions of the invention will be formulated in the forms conventionally used for topical administration: preferentially in the form of patches and sticking plasters, but also in formulations such as cream, cream-gel, gel, spray or powder, depending on the nature of the various ingredients used, employing techniques and preparation methods known to the skilled person.

According to a further preferred aspect, the compositions of the invention will be formulated in the form of patches mainly consisting of hydrocolloids rich in water, polyvinyl alcohol and sodium alginate.

The compositions according to the present invention can be prepared according to conventional methods well known in pharmaceutical and cosmetic technology.

Further characteristics and advantages of the invention will emerge more clearly from the following description of some non-limiting examples of compositions according to the invention.

Example 1

A composition was prepared in the form of patches having 0.02% w/v resveratrol and 0.1% w/v essential oil of *Eugenia caryophyllata* as active ingredients.

Due to its particular molecular structure, this matrix is able to contain a large quantity of water which, as it evaporates during application, cools the treated part of the body and causes the active ingredients to permeate through the skin by osmosis. In this way the substances are released rapidly, thus allowing treatments for which a fast action is required.

The patch is made as follows.

Water, preservatives, carboxymethylcellulose sodium and polyvinyl alcohol, in the quantities indicated in the Batch Record, are introduced into a stainless steel mixer. The mixture is heated under medium stirring. The functional substances are added after cooling, under continual stirring. Sodium alginate is then added, and the mixture is mixed until gelling is complete.

The semisolid gel obtained is spread between a layer of PET and a layer of NWF (non-woven fabric) after setting all the machine parameters (weight of spread and spreading rate).

At the output from the spreading machine, the semi-manufactured product is cut into sheets of the appropriate size (as indicated in the Batch Record), and collected in plastic boxes.

The sheets are punched to obtain patches of the required shape and size.

Example 2

According to the process described in Example 1, a composition was prepared in the form of patches containing 0.04% w/v resveratrol, 0.1% w/v essential oil of *Eugenia caryophyllata*, 3% w/v polidocanol and 1% w/v menthyl lactate as active ingredients.

Example 3

A composition in the form of a cream or gel was prepared. The active ingredients, such as 0.02% w/v resveratrol and 0.1% w/v essential oil of *Eugenia caryophyllata*, were mixed to obtain a single homogenous solution.

They were then added to an aqueous solution at the temperature of 70/80° C. At this point a mixture, mainly consisting of excipients and vegetable or animal fat, was added at 65/75° C. to obtain the final cream or gel. The cream or gel was then mixed to obtain a homogenous final paste ready for pack packaging.

Example 4

According to the process described in Example 1, a composition was prepared in the form of patches containing 0.1% w/v resveratrol, 0.1% w/v essential oil of *Eugenia caryophyllata*, 3% w/v polidocanol and 1% w/v menthyl lactate as active ingredients.

Example 5

According to the process described in Example 1, a composition was prepared in the form of patches containing 0.1% w/v resveratrol and 0.1% w/v essential oil of *Eugenia caryophyllata* as active ingredients.

Example 6

According to the process described in Example 1, a composition was prepared in the form of patches containing 0.5% w/v resveratrol, 0.1% w/v essential oil of *Eugenia caryophyllata*, 3% w/v polidocanol and 1% w/v menthyl lactate as active ingredients.

Example 7

According to the process described in Example 1, a composition was prepared in the form of patches containing 0.5% w/v resveratrol and 0.1% w/v essential oil of *Eugenia caryophyllata* as active ingredients.

Pharmacological Section

The dermatological patch described in Example 1, with a very low dose of the active ingredients, was tested on patients with inflamed seborrhoeic keratosis to be treated by curettage.

The aim was to measure the antinociceptive effect of the patch, recording whether its use made local anaesthesia, which must usually be performed for larger growths, superfluous.

The totally unexpected finding after the use of the patch was the lytic effect on itching only 10 minutes after the application, an effect which was maintained for at least 24 hours, as appears from the results reported below under the heading Clinical Trial.

This result is even more unexpected in view of the short time taken for the effect to be manifested (10 minutes), the low concentration of the active ingredients, and their low efficacy on analgesia (pain) and inflammation.

In fact, the antinociceptive and anti-inflammatory effects may partly explain the lytic properties of the patch on itching; however, these effects were mild and short-lived, and in any event different nerve pathways are now recognised between pain and itching, and consequently a different pathophysiology and different treatment.

Finally, anti-inflammatories and antihistamines generate a high degree of dissatisfaction as a treatment for itching.

On the basis of the clinical trial, no adverse effects and/or undesirable effects were recorded, demonstrating the high tolerability of the product resulting from its safety in use. This factor combines with the benefits of the product to distinguish it from all other current topical and/or systemic treatments, which are not devoid of side effects and undesirable effects.

Clinical Trial

Itching Caused by Inflamed Seborrhoeic Keratosis

The dermatological patch described in Example 1, measuring 5 cm×6 cm, was applied for approx. 20 minutes to a patient with inflamed seborrhoeic keratosis.

A partial anti-inflammatory effect was observed, demonstrated by the reduction of the perilesional "anaemic halo" effect, and a mild anaesthetic effect which, though detected, was not sufficient to meet the patients' expectations or to make local anaesthesia superfluous.

The totally unexpected finding following the use of the patch was its lytic effect on itching: the patient spontaneously stated that itching had completely disappeared only 10 minutes after the application. It is the unpleasant itching that causes patients with inflamed seborrhoeic keratosis to ask their doctors for curettage.

Itching Caused by Lichen Simplex

The dermatological patch described in Example 1, measuring 5 cm×6 cm, was tested on two patients with lichen simplex. The patch was applied to the lesion and left until it spontaneously fell off due to drying (maximum residence time: 30 minutes). The treatment was performed 3 times at 24-hour intervals.

Both patients reported the lytic effect of the patch on the itching sensation approx. 10 minutes after its application; moreover, this effect lasted for at least 24 hours, i.e. until the next patch was applied.

When the patients were examined on the third day, a partial reduction of the inflammatory infiltration that typically accompanies the clinical syndromes in question was observed.

In all the cases examined, perfect tolerability of the product was observed, and no adverse effects or discomfort of any kind were reported.

REFERENCES

1) E. Weisshaar and F. Dalgard, —Epidemiology of Itch: Adding to the Burden of Skin Morbidity, Acta Derm Venereol 2009; 89: 339-350.
2) Ikoma A, Steinhoff M, Stander S, Yosipovitch G, SchmelWz M. —Neuronal sensitization for histamine-induced itch in lesional skin of patients with atopic dermatitis. Arch Dermatol. 2003 November; 139(11): 1455-8.
3) Yvette A. Tivoli, Do; Brichard M. Rubenstein M D, —Pruritus: An Updated Look at an Old Problem, J Clin Aesthet Dermatol. 2009 July; 2(7): 30-6.
4) Greaves Malcolm W. Recent Advances in Pathophysiology and Current Management of Itch. Review Article. Annals Academy of Medicine Singapore 2007; 36:788-92.
5) Rukwied R et al. Mast cell mediators other than histamine induce pruritus in atopic dermatitis patients: a dermal microdialysis study. —Br J Dermatol 2000; 142: 1114-1120.
6) Baur J A and Sinclair D A. Therapeutic potential of resveratrol: the in vivo evidence. Nature Reviews. Drug Discovery. Volume 5. June 2006.
7) Gentilli, M. et al. Resveratrol decreases hyperalgesia induced by carrageenan in the rat hind paw. Life Sci. 68, 1317-1321 (2001).
8) Torres-Lopez, J. E. et al. Comparison of the antinociceptive effect of celecoxib, diclofenac and resveratrol in the formalin test. Life Sci. 70, 1669-1676 (2002).
9) Granados-Soto, V., Arguelles, C. F. & Ortiz, M. I. The peripheral antinociceptive effect of resveratrol is associated with activation of potassium channels. Neuropharmacology 43, 917-923 (2002).
10) Chaieb K et al. The chemical composition and biological activity of clove essential oil, *Eugenia caryophyllata* (Syzigium aromaticum L. Myrtaceae): a short review. Phytother Res. 2007 June; 21(6):501-6.
11) Amorim A C et al. Antinociceptive and hypothermic evaluation of the leaf essential oil and isolated terpenoids from *Eugenia uniflora* L. (Brazilian Pitanga). Phytomedicine 16 (2009) 923-928.

The invention claimed is:

1. A method for the treatment of itching in a subject in need thereof comprising the topical administration to said subject of a formulation comprising active ingredients within the following weight/volume percentages:
   a) resveratrol: 0.01% to 10%;
   b) *Eugenia caryophyllata* essential oil: 0.01% to 2%.

2. The method according to claim 1, wherein the formulation comprises the active ingredients within the following weight/volume percentages:
   a) resveratrol: 0.05% to 0.2%;
   b) *Eugenia caryophyllata* essential oil: 0.02% to 0.2%.

3. The method according to claim 1, wherein the formulation is in the form of a patch, cream, cream-gel, gel, spray or powder.

4. The method according to claim 3, wherein the formulation is in the form of a patch.

5. The method according to claim 1, wherein the formulation comprises the active ingredients within the following weight/volume percentages:
   a) resveratrol 0.02%; and
   b) *Eugenia caryophyllata* essential oil: 0.1%.

* * * * *